United States Patent [19]

Ovshinsky et al.

[11] 4,340,662
[45] Jul. 20, 1982

[54] TELLURIUM IMAGING COMPOSITION

[75] Inventors: Stanford R. Ovshinsky, Bloomfield Hills, Mich.; Leon F. Hines, Hazleton, Pa.; Ronald W. Citkowski, Pleasant Ridge; Terry T. Yu, Mt. Clemens, both of Mich.

[73] Assignee: Energy Conversion Devices, Inc., Troy, Mich.

[21] Appl. No.: 277,720

[22] Filed: Jun. 26, 1981

Related U.S. Application Data

[63] Continuation-in-part of Ser. No. 73,699, Sep. 10, 1979, abandoned.

[51] Int. Cl.$^3$ .......................... G03C 1/00; G03C 5/24
[52] U.S. Cl. .................................... 430/270; 430/495; 430/292; 430/296; 430/494; 430/942; 430/346
[58] Field of Search ............... 430/269, 296, 942, 292, 430/494, 495, 402, 270, 346

[56] References Cited

U.S. PATENT DOCUMENTS

| | | | |
|---|---|---|---|
| 3,147,117 | 9/1964 | Wainer et al. | 430/332 |
| 3,527,639 | 9/1970 | Moraw | 430/340 |
| 3,579,342 | 5/1971 | Strilko | 430/340 |
| 3,700,448 | 10/1972 | Hillson et al. | 430/495 |
| 3,734,733 | 5/1973 | Poot et al. | 430/495 |
| 3,819,377 | 6/1974 | Klose et al. | 430/346 |
| 3,846,131 | 11/1974 | Lohmann et al. | 430/373 |
| 4,066,460 | 1/1978 | Chang et al. | 430/495 |
| 4,106,939 | 8/1978 | Chang et al. | 430/495 |
| 4,142,896 | 3/1979 | Chang et al. | 430/495 |
| 4,148,659 | 4/1979 | Vuyts et al. | 430/338 |

FOREIGN PATENT DOCUMENTS

| | | | |
|---|---|---|---|
| 854193 | 11/1977 | Belgium | 430/495 |
| 863052 | 7/1978 | Belgium | 430/495 |
| 2436132 | 2/1975 | Fed. Rep. of Germany | 430/495 |

OTHER PUBLICATIONS

Sprague et al., Photographic Science and Engr., V. 8, No. 2, (1964), pp. 91-103.
Ovshinsky et al., "Non-Silver Photographic Processes", edited by Cox, (Academic Press, 1975), pp. 61-70.
Fotland, "Optically Developed Free-Radical Photosensitive Materials", Journal of Photographic Science, V. 18, (1970), pp. 33-40.
Ovshinsky, "Amorphous Materials as Optical Information Media", Journal of Applied Photographic Engr., V. 3, No. 1, (1977), pp. 35-39.

*Primary Examiner*—Won H. Louie, Jr.
*Attorney, Agent, or Firm*—Brumbaugh, Graves, Donohue & Raymond

[57] ABSTRACT

This application relates to an imaging composition employing a tellurium compound sensitive to activating radiation. Such imaging compositions have been disclosed in a number of earlier patents, such as U.S. Pat. Nos. 4,142,896, 4,066,460 and 4,106,939. This application discloses improvements in masked reducing agents for such compositions. The improved masked reducing agents are compounds of the formulae

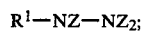

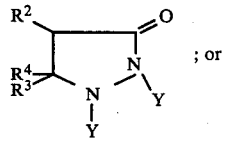

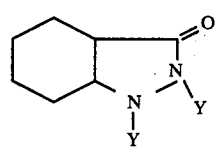

wherein Y is hydrogen or

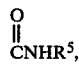

said compound containing at least one

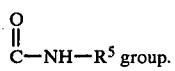

group.

65 Claims, No Drawings

TELLURIUM IMAGING COMPOSITION

This application is a continuation-in-part of our co-pending application Ser. No. 073,699, filed on Sept. 10, 1979 now abandoned.

This application relates to an improved imaging composition system employing tellurium compounds sensitive to activating energy.

THE PRIOR ART BACKGROUND

Various methods are known for producing images or duplicates of images. The imaging materials used are, in certain cases, particular inorganic compounds and, in other cases, particular organic compounds. Some of these heretofore known methods employ mixtures of inorganic compounds such as silver halide with one or more particular types of organic compounds as sensitizers.

A new photographic process using tellurium compounds to provide the image is disclosed in U.S. Pat. No. 4,142,896. In accordance with U.S. Pat. No. 4,142,896, an emulsion is formed using certain reducible precursor in a binder suitable for forming a film-like coating on a substrate. The film prepared therefrom is exposed imagewise to activating energy and may be thereafter developed as is known in the art hereinafter described. Heat development is preferred.

Some tellurium compounds described for use in the photographic process of U.S. Pat. No. 4,142,896 may be represented, for example, by the formula:

$$R_x\text{-}Te\text{-}X_y$$

in which R is an organic radical containing at least one carbonyl group, X is halogen, preferably chlorine, and X is 1, 2 or 3, and x+y=4. The organic radical R may be either two independent radicals or may be joined together to form a cyclic compound. Another group of compounds mentioned in U.S. Pat. No. 4,142,896 are organic tellurium compounds which may be considered or characterized as tellurium tetrahalide adducts of ethyleneic or acetyleneic hydrocarbons. Some of such compounds can be represented by the formulae:

$$X\text{—}R\text{—}\underset{\underset{X}{|}}{\overset{\overset{X}{|}}{Te}}\text{—}R_1\text{—}X$$

and $$(X\text{—}R)_n\text{—}Te\text{—}X_n$$

wherein R and $R^1$ are each the residue of an ethyleneic hydrocarbon, and X is a halogen, preferably chlorine.

Another broad category of photosensitive tellurium compounds which have been found useful are halogenated tellurium compounds, such as compounds of the formula $$TeCl_nBr_m$$

where n is an integer from 2 to 4, and n+m=4. The use of such halogenated tellurium compounds in imaging processes is disclosed in U.S. Pat. No. 4,066,460 to Chang et al.

Still another category of useful tellurium compounds are described in U.S. Pat. No. 4,106,939. These compounds are tellurium tetrahalide adducts of aromatic amines in which the nitrogen attached directly or indirectly to the aromatic ring is substituted by alkyls of 1–4 carbon atoms, the adduct being free of diazo groups.

The tellurium compounds such as the foregoing may be employed in conjunction with a reductant precursor which serves as a sensitizer. The reductant precursor is a compound which, under the influence of activating energy, will absorb radiation energy and abstract labile hydrogen from an appropriate hydrogen donor to become a strong reducing agent. The strong reducing agent reduces the tellurium compound, which results in a change in optical density suitable for recording information. In general terms, the foregoing reaction may be represented by the following mechanism:

$$PQ \xrightarrow{h\nu} {}^1PQ \longrightarrow {}^3PQ$$

$$^3PQ + 2RH \longrightarrow PQ \cdot H_2 + R\text{—}R$$

$$(R_1)_2 \cdot Te \cdot X + 2PQ \cdot H_2 \longrightarrow 2PQ + 2R_1H + Te + 2HX$$

wherein PQ is the reductant precursor sensitizing agent; $^1PQ$ is the first excited singlet state thereof; $^3PQ$ is the triplet state thereof; RH is the hydrogen donor; $PQ.H_2$ is the reductant precursor in its reduced state; and $(R_1)_2.Te.X_2$ is the reducible tellurium image-forming compound.

In this connection, it should be noted that the hydrogen donor need not be specifically provided, although a variety of alcohols can be used if desired. In the absence of a specially provided hydrogen donor, the labile hydrogen can sometimes be abstracted from the organic resins used as binders. In other cases, the sensitizer can be its own hydrogen donor, and this is known to be the case with at least one preferred sensitizer, namely, isoproxynaphthoquinone.

A modification of the tellurium photographic process is described in Belgian Patent No. 854,193, where certain diols of the formula $$R_{10}\text{—}CHOH\text{—}Z\text{—}CHOH\text{—}R_{11}$$

may be employed as the hydrogen donor for use in conjunction with the photosensitizer described above. In the foregoing formula, $R_{10}$ and $R_{11}$ represent hydrogen and various organic substituents. Z may be a direct carbon-carbon linkage between the two hydroxy-substituted carbon atoms, or may be any of various linking groups. Reference is made to Belgian Patent No. 854,193 for a fuller description of the diols referred to. In the Belgian patent, these diols are said to serve as hydrogen donors. Subsequent research has suggested that this is not completely accurate. In fact, a major portion of the diol appears to form a complex with the tellurium compound.

This finding has led to the discovery of diols of the general formula $$R\text{—}O\text{—}CH_2CHOH\text{—}CH_2OH$$

which has improved characterisitcs when used in tellurium-based photographic films.

The radical R may be a simple aliphatic group (for example, alkyl or alkenyl). Alternatively, the radical R may contain a carbonyl group (for example, an acyl radical). Preferably, however, the radical R is aromatic. Best results are obtained where the aromatic ring is separated from the ether oxygen by one methylene grouping. A more complete description of these diols is contained in co-pending application Ser. No. 073,700 filed Sept. 10, 1980.

Still another modification in the use of tellurium compounds as photosensitive agents involves what is known as a "masked reducing agent." A number of compounds are known, such as phenidone, which will reduce organo-tellurium compounds. The reducing capacity of such compounds may be "masked"—i.e., inhibited—by appropriate substitution. In such cases, if the substituent is one which can be cleaved by the reaction products liberated upon the photoreduction of the tellurium compound, the masked-reducing agent can be used to amplify the photo-response through the mechanism:

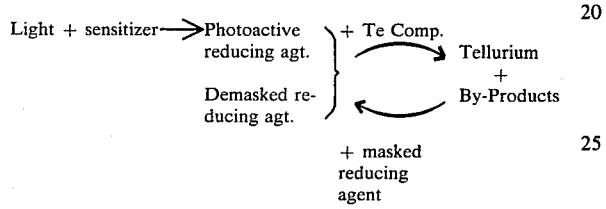

Since the tellurium compounds commonly used release hydrogen halides (particularly hydrogen chloride) as by-products of the reduction reaction, and the reducing agents, such as phenidone, are amino compounds, the masking agents most effectively employed are compounds which will convert the amino nitrogen into an amide. A typical masked reducing agent thus is the compound:

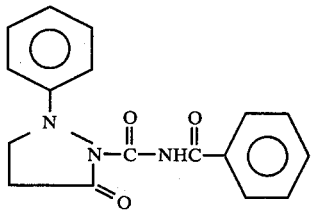

A more complete description of the masked reducing agent may be found in Belgian Patent No. 863,052, and reference thereto is made for an additional description thereof.

In practice, the foregoing ingredients, i.e., a tellurium derivative, a reductant precursor, and the optional ingredients such as the glycol and a masked reducing agent, are combined in a suitable matrix to form an emulsion which is supported by an appropriate carrier. A latent image is formed by exposure to an appropriate imaging energy (for example, a light image). The latent image is thereafter developed by heating the exposed film as described in U.S. Pat. No. 4,142,896.

Alternately, the latent image may be induced by using an electron beam or an electric current as the activating energy. Since electrons so introduced into the film are capable of acting directly on the tellurium compound when such activating energy is used, the reductant precursor can be omitted from the composition.

Other forms of activating energy will be recognized by those skilled in the art, and can also be applied under appropriate conditions.

THE INVENTION

The present invention concerns an improvement in the above-described organo-tellurium system for photosensitive emulsions. More specifically, we have found new masked reducing agents of the general formulae:

$R^1-NZ-NZ_2$;

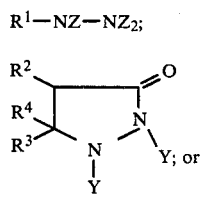

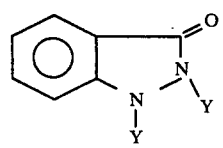

wherein Y is hydrogen or

said compound containing at least one

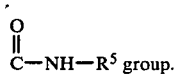 group.

In the foregoing formulae, $R^1$ may be alkyl, alkanoyl, alkoxycarbonyl, phenyl, benzyl, benzoyl, nitrophenyl, benzylcarbonyl, diphenylmethyl, diphenylethyl, or diphenylpropylcarbonyl, or aminocarbonyl. $R^2$, $R^3$ and $R^4$ each, and independently, may be hydrogen, alkyl or phenyl and amino. $R^5$ may be phenyl, nitrophenyl, halophenyl, alkyl, mono-, di- or tri-halocetyl, benzoyl, alkylphenyl, or alkyl-p-isocyanophenyl. The masking group may be substituted at either one or both of the amino nitrogen sites of the reducing agent. The alkyl groups referred to above may contain up to seven carbon atoms. The novel mask-reducing agents of the present invention provide unexpected improvements in film speed, background density or both.

These compounds are conveniently accessible through reaction of the parent hydrazine or pyrazolidine with an isocyanate of the formula

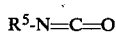

Representative compounds of the foregoing are the following:

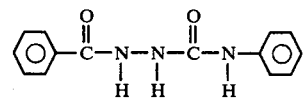

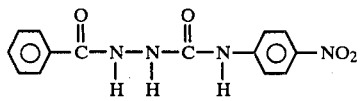

-continued

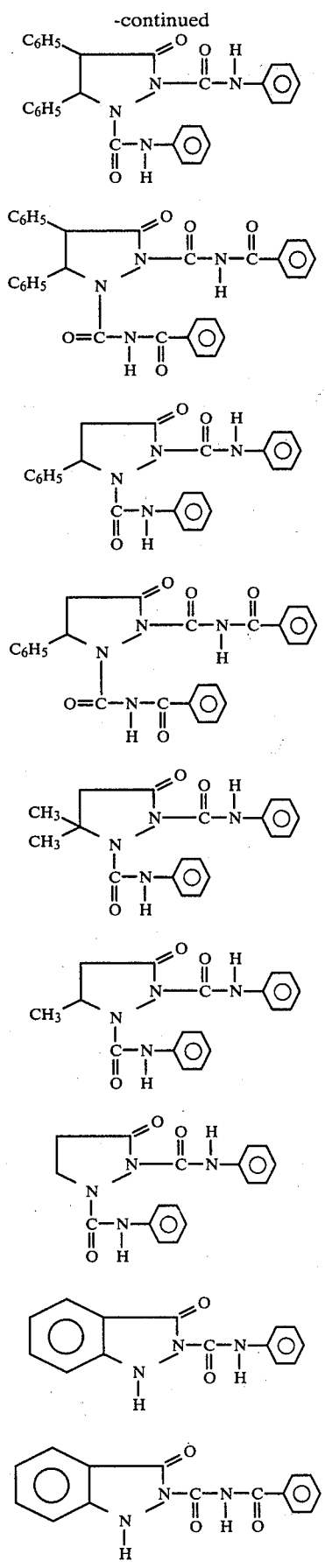

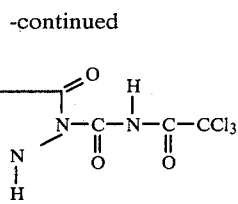

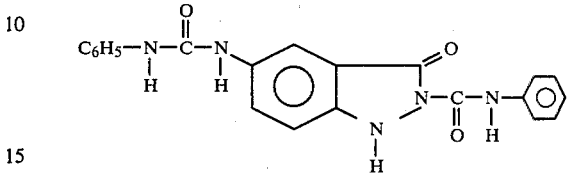

DETAILED DESCRIPTION OF EMULSIONS ACCORDING TO THE PRESENT INVENTION

An emulsion formulated in accordance with the present invention contains a tellurium compound, a reductant precursor, and an appropriate binder, and a carrier on which a photosensitive film can be formed, and a masked reducing agent of the above description. Optionally, a diol is provided, preferably a glyceryl compound of copending application Ser. No. 073,700 filed Sept. 10, 1979.

The image-forming tellurium. A number of image-forming tellurium compounds are described in the prior art and such compounds are generally useful in the present invention. In general, the present invention contemplates using these and other tellurium compounds which undergo analogous reduction reactions in the presents of a reductant precursor as hereinafter described.

It has been found that many tellurium compounds possess certain properties which adapt them especially for use in imaging processes. In general, these are compounds from which, as a result of the imaging and developing steps generally referred to above, elemental tellurium is deposited from the tellurium compounds. Tellurium is chain-forming in character, and it is generally deposited from the tellurium compounds useful for photographic purposes (preferably including thin needles), the compounds being capable of rapid nucleation and growth as crystallites, which crystallites grow as chains and largely or mainly as needles. Such chains or needles are opaque and are characterized by excellent light scattering properties to produce good optical density observed after thermal or other development.

Effects which may involve oxide formation are substantially restricted to surface effects as distinguished from effects which cause degradation through the bodies of the needles or chains.

Preferably, the tellurium imaging compound is an organo-tellurium compound such as disclosed in U.S. Pat. No. 4,142,896 of Chang et al. These compounds are organic tellurium compounds which inherently possess sensitizer properties (and/or may be mixed with a separate sensitizer) in which the tellurium is linked directly to at least one carbon atom or the organic radical of the organo-tellurium material, the organic tellurium compound being of one structure and having a detectable characteristic which is capable of undergoing a change in response to the application of imaging energy in the form of particle or wave radiation to produce a material of different structure having another detectable characteristic. The material having a different structure and different detectable characteristics resulting from the imaging step is sometimes referred to as the "image-forming compound".

A particularly advantageous subgroup of the imaging organo-tellurium compounds utilized in the practice of the present invention comprises organic compounds which contain an organo radical and halogen attached directly to the tellurium atom, there being at least one carbonyl group in the organo radical. Certain of them are adducts of tellurium halides, notably tellurium tetrachloride, with organic compounds, notably ketones or similar chromophores, containing at least one carbonyl group in the organic compound. They may, thus, be considered or characterized as organo-tellurium compounds or adducts containing halogen, namely, chlorine, bromine, iodine, and fluorine, attached directly to the tellurium atom. Most of this particular class or group of said imaging compounds have two carbonyl-containing organo radicals. Those which are especially useful in the practice of the present invention have chlorine as the halogen but, in certain cases, although generally less satisfactory, other halogens can be present. The imaging compounds should be selected to be soluble or homogeneously dispersible in any particular matrix material which may be utilized, as is described hereafter. Many of this group of imaging organo-tellurium compounds may be represented by the formula $R_x$-Te-Hal$_y$ 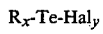

where R is an organo radical containing at least one carbonyl group, Hal is halogen, especially chlorine, x is 1, 2 or 3, and x+y=4, subject to the proviso that Te is linked directly to carbon in an organo radical. Preferably, x is 2 or 3.

Others can be represented by the formula $R_2$-Te-Hal$_4$ 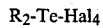

where R is a carbonyl-containing organic radical, and Hal is halogen.

The R radical can be aliphatic, cycloaliphatic or aromatic (mononuclear or dinuclear) or a combination thereof and may contain one or more hetero atoms in the chain or rings. It may be unsubstituted or substituted by various organic or inorganic radicals, which may assist in or at least do not interfere with the desired imaging effect, illustrative of such radicals being $C_1$-$C_6$ alkyl, corresponding oxyalkyl radicals, acetyl, nitro, $C\equiv N$, Cl, Br, F, etc. Generally speaking, the aforesaid organo-tellurium imaging compounds which contain a trihalide group as, for instance, acetophenone tellurium trichloride, tend to have relatively low melting points ($\sim 70°$–$80°$ C.), and are more hygroscopic and less stable than those generally similar compounds containing two halogen atoms and, therefore, such trihalides are less desirable for use in the practice of the present invention.

A more limited class of this particular subgroup of imaging organo-tellurium compounds may be represented by the formula (Ar-CO-CH$_2$)$_2$Te-Hal$_2$ 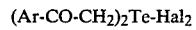

where Ar is an aromatic hydrocarbon radical, which may be substituted or unsubstituted, as indicated above, and Hal is halogen, especially chlorine. This subgroup of compounds, particularly where Hal is chlorine, represents especially advantageous embodiments of the invention, with respect to the imaging organo-tellurium compounds which are used in the practice of the present invention.

Another subgroup of imaging organo-tellurium compounds, useful in the practice of and contemplated by the present invention, which do not contain a carbonyl group in an organo radical but in which tellurium is linked directly to carbon are compounds which may be considered or characterized as tellurium tetrahalide adducts of ethylenic or of acetylenic hydrocarbons. These compounds are generally conveniently produced by reacting 1 to 2 moles, particularly 2 moles, of the ethyleneic or acetyleneic hydrocarbon with 1 mole of tellurium tetrahalide, especially preferred for such use being TeCl$_4$. Certain of such compounds can be represented by the formulae:

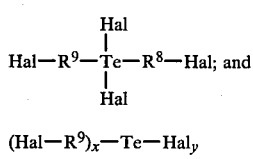

(Hal—R$^9$)$_x$—Te—Hal$_y$ where R$^8$ and R$^9$ are each the residue of an ethyleneic hydrocarbon, for instance, an alkene or a cycloalkene, Hal is chlorine, bromine or iodine, especially chlorine, x is 1 to 3, and x+y=1.

Illustrative of the ethyleneic and acetyleneic hydrocarbons which can be adducted with tellurium tetrahalides to produce such imaging organo-tellurium compounds are propylene; butene-1; isobutylene; butene-2; 2,3-dimethyl-2-butene; 3,3-dimethyl-1-butene; 2,4-dimethyl-1-pentene; 4,4-dimethyl-1-pentene; 2,5-dimethyl-3-hexene; dipentene; 1,1-diphenylethylene; 1-heptene; 1-hexene; 2-methyl-1-hexene; 3-methyl-1-hexene; 4-methyl-1-hexene; 2-ethyl-1-hexene; 2-isopropyl-1-hexene; 2-methyl-1-pentene; 2-methyl-2-pentene; 2-ethyl-2-pentene; 3-methyl-1-pentene; piperylene; vinylcyclohexene; vinylcyclopentene; 2-vinylnaphthalene; 1,2,4-trivinylcyclohexene; 4-methyl-1-cyclohexene; 3-methyl-1-cyclohexene; 1-methyl-1-cyclohexene; 1-methyl-1-cyclopentene; cycloheptene; cyclopentene; cyclohexene; 4,4-dimethyl-1-cyclohexene; 2-methylbutene-1; 3-methylbutene-1; and 1-octene; lower alkyl and lower alkoxy derivatives of various of the alkenes such as cyclohexene; 1-pentyne; 2-pentyne; 1-hexyne; and 3-methyl-1-butyne.

The preparation of the aforementioned organic tellurium compounds as well as many examples thereof are more fully set forth in U.S. Patent No. 4,142,696, which is hereby incorporated by reference.

As indicated above, tetrahalides of tellurium in which the halide is at least one member selected from the group consisting of chlorine and bromine are also useful as the image-forming material in the present invention. Such tellurium halides are fully described in U.S. Pat. No. 4,066,460, the specification of which is hereby incorporated by reference. Certain of these imaging materials can be represented by the formula TeCl$_n$Br$_m$ 

where n is an integer from 1 to 4 and m+n=4. Typical tellurium tetrahalides which may be used are TeCl$_4$; TeCl$_2$Br$_2$; and TeClBr$_3$. TeCl$_4$ is especially useful. Reference is made to U.S. Pat. No. 4,066,460 for a fuller description of these tellurium tetrahalides and their use as image-forming compounds.

Still another group of image-forming compounds are certain compounds derived from tellurium tetrahalides which are described in U.S. Pat. No. 4,106,939 to Chang et al. These involved compounds are adducts of tellurium tetrahalide with aromatic amines exemplified by the tellurium tetrachloride adduct of dimethylaniline, which adduct is free of diazo groups. More specifically, these tellurium tetrahalide adducts are formed by combining a tellurium tetrahalide with an aromatic amine in which nitrogen attached directly or indirectly to the aromatic radical is substituted by alkyls containing from 1 to 4 carbon atoms, the imaging organo-tellurium material being free from diazo groups.

These aromatic amine adducts of the tellurium tetrahalides are fully described in U.S. Pat. No. 4,106,939 to Chang et al.; the disclosure thereof is hereby incorporated by reference.

The active tellurium compounds may, if desired, be formed in situ, for example, by using a tellurium oxide or a tellurium salt in combination with a suitable organic compound. Sometimes the in situ formation is promoted by the presence of an acid. For example, tellurium oxide or alkali metal tellurates may be combined with one of the glycols described below to form a tellurium-organic compound complex which is active. It is believed that the reaction is analogous to the reaction between organic tellurium compounds such as described above and a diol. Preliminary information suggests that the reaction is favored by an acidic medium. Small amounts of an acid such as anhydrous hydrogen chloride may be added. Alternatively, halogen-containing tellurium compounds will provide the requisite acidity.

The reductant precursor: In addition to the tellurium image-forming compound, the imaging systems of the present invention may include a reductant precursor, or sensitizer, which, as described above, is a compound that, under the influence of activating energy, has the property of extracting labile hydrogen from a hydrogen donor to become a reducing agent with respect to the image-forming tellurium compound. The activated reducing agent then reduces the tellurium compound to produce the desired image. The hydrogen donor may be an external source of hydrogen such as an alcohol specifically provided for the purpose. However, the hydrogen donor may equally well be an appropriate group which is a part of the molecular structure of the reductant precursor.

Preferred reductant precursors useful in the present invention are quinones, particularly 2-isopropoxynapthoquinone; 9,10-phenanthenequinone; and 2-t-butylanthraquinone. Benzophenone, although not a quinone, is also useful as a reductant precursor, as are a number of the simpler ketones.

A factor of importance in the selection of reductant precursors is the spectral range to which the reductant precursors respond. For that reason, the simple ketones are not generally useful for recording visible light since their spectral sensitivity is in the far ultraviolet region. Other reductant precursors and their approximate spectral sensitivity ranges are as follows:

| Reductant Precursor | Spectral sensitivity range (nm) |
|---|---|
| 9,10-phenanthrenequinone | 200–400–500 |
| | U.V. Visible |
| 1,1'-dibenzoylferrocene | 400–600 |
| 1-phenyl-1,2-propanedione | 400–500 |
| 2-hydroxy-1,4-naphthoquinone | 400–500 |
| Benzil | 400–450 |
| Furil | 400–480 |
| Diacetylferrocene | 400–450 |
| Acetylferrocene | 400–450 |
| 1,4-bis(phenyl glyoxal) benzene | 400–500 |
| o-naphthoquinone | Up to about 560 |
| 4,5-pyrinequinone | Up to about 530 |
| 4,5,9,10-pyrinequinone | Up to about 550 |

The following are illustrative reductant precursors which are sensitive in the range of up to about 400 nm and, therefore, are useful only in the ultraviolet range: Benzophenone; acetophenone; 1,5-diphenyl-1,3,5-pentanetrione; ninhydrin, 4,4'-dibromobenzophenone; and 1,8-dichloroanthraquinone.

Various other reductant precursors can be utilized, particularly those of the type of substituted or unsubstituted polynuclear quinones, of which class some have been mentioned above, and others of which are 1,2-benzanthraquinone; 2-methylanthraquinone; 1-chloroanthraquinone; 7,8,9,10-tetrahydronaphthacenequinone; 9,10-anthraquinone; and 1,4-dimethylanthraquinone. It will be understood that not all reductant precursors will be effective or equally effective, with each given imaging material, even taking into account the utilization of imaging energy in the sensitivity range of the reductant precursor employed and that suitable selections of combinations of particular imaging materials and particular reductant precursors will be required to be made for achieving desirable or optimum results. Such selections, however, can be made relatively readily.

In general, in connection with the foregoing matters, it may be noted that reductant precursors have $\eta\pi^*$ states, both singlet and triplet, of lower energies than $\pi,\pi^*$ states and, at least in most cases, compounds which have their $\pi,\pi^*$ states of lowest energy will not be photosensitively effective, although, in certain limited cases, compounds which fulfill the test of having lower energy $\eta \rightarrow \pi^*$ than $\pi \rightarrow \pi^*$ transitions do not function as reductant precursors. However, the above consideration is, in the main, an effective one for determining in advance whether a given compound will function as a reductant precursor for use in the practice of the present invention. In any event, a simple preliminary empirical test in any given instance can readily be carried out if necessary by preparing a test emulsion using the desired imaging compound and reductant precursor.

In some cases an external sensitizer is not needed. For example, at wavelengths in the region of 250–300 nm most organotellurium compounds are directly photolyzed; and, certain other tellurium compounds, notably the halides, are sensitive to the blue portions of the visible spectrum. When imaging is to be accomplished by electrons, no additional sensitizer is needed, since the electron effects direct decomposition of the imaging material.

The Diol: In accordance with the present invention, there may also be included a diol which reacts with the tellurium compound to form an active intermediate complex. While the chemistry of the complex is not well understood, we believe that, in general, the complex requires approximately 2 moles of diol for each mole of tellurium. Preferably, the diol, when present, is used in excess of the minimum amount to form a complex since the diol will also function as a source of labile hydrogen to provide the source of hydrogen required in the reaction of the reductant precursor.

While the present invention involving the use of novel masked reducing agents can be practiced without the inclusion of a diol, the presence of a diol is much preferred. We have found that the presence of a diol serves to markedly reduce the optical density of unexposed areas (i.e., thus increasing the contrast between the exposed and unexposed areas) particularly when a masked reducing agent is present. Thus, while masked reducing agents can be used in the absence of a diol, tellurium film compositions containing masked reducing agents tend to have a relatively high optical density in the unexposed areas because the reducing capacity of the masked reducing agent is not fully inhibited by the masking group.

One group of diols which may be used in formulating imaging compositions are diols of the formula $$R^{10}-\underset{\underset{OH}{|}}{\overset{\overset{H}{|}}{C}}-Z-\underset{\underset{OH}{|}}{\overset{\overset{H}{|}}{C}}-R^{11}$$

wherein each of $R^{10}$ and $R^{11}$ independently represents hydrogen, a hydrocarbon group, including straight chain, branched chain and cyclic hydrocarbon groups, hydroxyalkyl groups, alkoxycarbonyl groups, cycloalkyl groups or aryl groups; and Z represents an arylene group (for example, phenylene), the group (—C≡C—), the group (—$CR^{12}$=$CR^{13}$)$_n$, wherein n represents a whole number, for example, 1 or 2, and each of $R^{12}$ and $R^{13}$ represents hydrogen or an alkyl group or taken from part of a carbocyclic or heterocyclic ring. Z also may be omitted—that is, the two hydroxy-substituted carbons are joined directly to each other. The following table illustrates a number of diols which may be used:

| No. of the Compound | $R^{10}$ | Z | $R^{11}$ | Boiling Point (BP) °C. or Melting Point (MP) °C. |
|---|---|---|---|---|
| 1 | H | — | H | BP 198 |
| 2 | 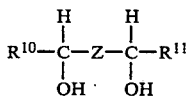 | — | H | MP 67 |
| 3 | H$_3$C— | — | H | BP 189 |
| 4 | H$_3$C— | — | —CH$_3$ | BP 183 |
| 5 | H | —C≡C— | H | MP 52–54 |
| 6 | H | | H | MP 112 |
| 7 | HO(CH$_2$)$_4$— | — | H | BP 178/5 mm Hg |
| 8 | $\underset{\underset{O}{\|\|}}{C_2H_5OC-}$ | — | $\underset{\underset{O}{\|\|}}{C_2H_5O-C-}$ | BP 280 |

A fuller description of the foregoing diols may be found in Belgian Patent No. 854,193, the disclosure of which is hereby incorporated by reference.

Preferably, however, the diol is of a more complex type than disclosed in the above-mentioned Belgian patent application. These more complex diols are the subject matter of co-pending application, Ser. No. 073,700 filed Sept. 10, 1979.

The preferred diols, as described in the aforementioned application Ser. No. 073,700, are compounds of the formula $$R^7\text{-O-CH}_2\text{-CHOH-CH}_2\text{OH}$$

In the foregoing compound, $R^7$ may be alkyl, acyl, thiazolinyl, alkenyl, phenyl, alkylphenyl, alkenylphenyl, hydroxyalkylphenyl, benzyl, alkylbenzyl, alkoxybenzyl, hydroxyalkylbenzyl, and halobenzyl and similar radicals.

The "thio" analogs of the foregoing compounds can be used (i.e., compounds in which the radical $R^7$ is joined to the glycerol residue by a thio linkage in place of the oxy linkage.

Preferred compounds of the foregoing structure are those in which the radical $R^7$ is benzyl or a substituted benzyl. The use of the diols of the foregoing structure has been found to be preferred since they are more effective in reducing the optical density of the unexposed areas than are the diols described in Belgian Patent No. 854,193.

Ancillary Ingredients: In addition to the foregoing principal ingredients of the present formulation, ancillary ingredients may be included for various purposes. Thus, for example, it has been found that certain materials enhance the shelf life of unexposed virgin dry film compositions of the present invention, and in certain instances, they also enhance the sensitivity of said film compositions. Illustrative embodiments of such additional or supplemental materials, which contain ether or polyether linkages in the molecules thereof, are such materials or polymers as polyethylene-20 sorbitan monolaurate; polyethylene-20 sorbitan monooleate; Polyox-10; Polyox-80; Polyox-750; polyethylene glycol-400 distearate; polyethylene glycol-600 distearate; poly (1,3-dioxolane); poly (tetrahydrofuran); poly (1,3-dioxepane); poly (1,3-dioxane); polyacetaldehydes; polyoxymethylenes; fatty acid esters of polyoxymethylenes; poly (cyclohexane methylene oxide); poly (4-methyl-1,3-dioxane); polyoxetanes; polyphenylene oxides; poly [3,3-bis (halomethyl) oxocyclobutane]; poly (oxypropylene) glycol epoxy resins; and copolymers of propylene oxides and styrene oxides. Such materials can be incorporated in the imaging film compositions in varying amounts, generally from 5 to 20% by weight of the solid imaging film compositions. In certain cases then enhance or prolong the shelf life or storage life, under given storage conditions, as much as 50% or even very substantially more timewise, and, as indicated, they also, in various cases, effectively increase film sensitivity.

Again, the inclusion in the imaging films of reducing sugars has been found, generally speaking, to bring about an enhancement in density of the image area (O.D. image-O.D. background), when the film is imaged as disclosed above and then developed, for instance, at about 120°–150° C. and for the order of about 15 seconds, especially where the imaging film is freshly prepared or not older than about a day after initial preparation. Such films, when exposed to imaging energy and then developed resulted in the production of a positive image (i.e., the optical density is greater in the non-exposed areas than in the exposed areas) in contrast to the negative working system which exists in the usual practice of the present invention. The inclusion of reducing sugars in the imaging compositions also enables development of the image, after exposure to imaging energy, to take place at lower temperatures, even at room temperatures, in a period of several hours, for instance, commonly in 10, 12 or 15 hours. The reducing sugars which can be employed are many, illustrative of which are dextrose, glucose, arabinose, erythrose, fructose, galactose, fucose, mannose and ribose. Especially effective are dextrose, arabinose, galactose, fucose and ribose. The reducing sugars can be used in variable amounts, but generally in equivalent amounts, or somewhat smaller or greater, in relation to the amount of imaging organo-tellurium materials in the imaging compositions.

It may be desirable in many cases to include a small amount of a silicone oil or similar material as is well known to aid in coating of smooth continuous films.

The matrix material: A film composition in accordance with the present invention is completed by dissolving the ingredients and optional ingredients described above in a suitable matrix. The matrix should be as concentrated as is practicable in the active ingredients, i.e., the least amount of matrix is preferably used. The amount of matrix should be sufficient as to just retain the various active ingredients in a solid solution. An additional quantity of matrix may be used, however, that obviously tends to dilute the concentration of active ingredients, thereby slowing down the photo-response of the film composition. The selection of matrix materials, of course, must be related to the active ingredients used so as to provide the maximum solubility for any particular composition.

The matrix materials, into which the imaging organotellurium materials, and the separate sensitizers when employed, are incorporated to produce the imaging film or coating, are solids at room temperature, and they can be selected from a relatively large number of materials. They should desirably be at least in part of amorphous character and it is especially desirable that they be glassy, polar amorphous materials having a glass transition temperature, which desirably should not exceed about 200° C. and may be as low as about 50° C., and, better still, should be within the range of about 80°–120° C. They are generally polymeric materials. Illustrative thereof are cyanoethylated starches, celluloses and amyloses having a degree of substitution of cyanoethylation of $\geq 2$; polyvinyl-benzophenone; polyvinylidene chloride; polyethylene terephthalate ("MYLAR"); cellulose esters and ethers such as cellulose acetate, cellulose propionate, cellulose butyrate, methyl cellulose, ethyl cellulose, hydroxypropyl cellulose, polyvinylcarbazole; polyvinyl chloride; polyvinyl methyl ketone; polyvinyl alcohol; polyvinylpyrrolidone; polyvinyl methyl ether; polyacrylic and polymethacrylic alkyl esters such as polymethyl methacrylate and polyethyl methacrylate; copolymer of polyvinyl methyl ether and maleic anhydride; various grades of polyvinyl formal resins such as so-called 12/85, 6/95 E, 15/95S, 15/95E, B-79, B-98, and the like, sold under the trademark "FORMVAR"-(Monsanto Company). Of especial utility is polyvinyl formal 15/95% which is a white, free flowing powder having a molecular weight in the range of 24,000–40,000 and a formal content expressed as percent polyvinyl formal of approximately 82%, possessing high thermal stability, excellent mechanical durability, and resistance to such materials as aliphatic hydrocarbons, and mineral, animal and vegetable oils. These polymeric materials or resins and their preparation are well known to the art. In addition to their functioning as carriers for and holding together in a unitary composition the imaging organo-tellurium materials, sensitizers and any other ingredients which may be incorporated into the imaging film or coating or layer and their functioning as dry or essentially dry film-forming materials to provide thin films and providing mechanical durability in the finished imaged film, at least many of them appear also to play a chemical or physical role in the imaging process by providing, importantly, a source of readily easily abstractable hydrogen and, thus, appear to play a significant role in the latent image formation mechanism, as discussed hereafter. In certain instances, it may be desirable to decrease the viscosity of the matrix, which can be done, by way of illustration, by the addition of certain plasticizers, for instance, dibutylphthalate or diphenylphthalate, which additions tend to result in the production of images desirably of higher optical densities but which, however, also tend to have the disadvantage of increasing background fogging.

It may be noted that matrix materials of the type which contain basic groups may complex with the imaging organo-tellurium materials and, therefore, to the extent that such complexing may occur, the use of such matrix materials should be avoided.

Formulation of Film Compositions: In the production of the films or thin layers of the imaging material compositions, which are generally prepared in the form of solutions or homogeneous dispersions and coated or laid down on a substrate, it is especially desirable to dissolve or homogeneously disperse the ingredients in an organic solvent. Illustrative of suitable solvents are methyl ethyl ketone (MEK), dimethylformamide (DMF), chloroform, tetrahydrofuran (THF), dimethylacetamide (DMA), dioxane, dichloromethane and ethylene dichloride, or compatible mixtures of such organic solvents or with other organic solvents. After the solution or homogeneous dispersion is filmed on a substrate in any suitable manner, the major proportions of such organic solvent or solvents are evaporated off, preferably at a relatively low temperature and, sometimes desirably, under subatmospheric pressures or in vacuo, until the film or coating is substantially dry to the touch, such dry-to-the-touch coating being especially desirable for handling and processing purposes. Although such films or coatings may be, generally speaking, dry to the touch, it should be understood that this does not mean that the film is free from organic solvent. Indeed, it has been found that it is frequently very desirable that the finished films or coatings, prior to exposure to imaging energy, contain a small percentage, commonly of the general order of about 2 to 3%, by weight of the film or coating, or organic solvent, for instance, dimethylformamide (DMF) since its presence appears to play a favorable role in the sensitivity of the system in relation to the latent image formation and/or ultimate image obtained after the development step. The elimination of all or essentially all of the DMF, or other organic solvent or solvents, from the virgin film prior to the imaging and development frequently leads to a decrease in sensitivity. In any event, in any given instance where drying of the virgin imaging film has been carried out to a point where essentially no organic solvent is present, and whereby sensitivity is unduly reduced, sensitivity can be increased or restored by adding a small amount of organic solvent to the film prior to exposing it to imaging energy.

The imaging film or coating thickness are variable but will usually fall within the range of about 1 to about 35 μm with about 5 to 15 μm generally being a good average. In thickness in terms of millimeters (mm), such may vary from about 0.0005 to about 0.05 mm, or much greater, such as from 0.05 to 5 mm, the selected thickness being dependent upon the particular use to which the imaging film is to be put.

The production of the imaging organo-tellurium materials, and the coating, handling and processing operations, to the extent which may be required, are carried out under appropriate light conditions, as those skilled in the art will readily understand. For instance, the formulation of the coating compositions and the coating and drying operations are conveniently carried out under amberlite filtered light (weak transmission at 550 nm). The dry film prior to imaging, is desirably stored in the dark. In certain cases, avoidance of contact of certain of the ingredients with certain metals may be in order where undesired reactions, such as reductions, may occur. In general, the vessels or containers, stirrers, etc., utilized should be made of glass or other vitreous materials or other materials inert to the coating ingredients to insure against contamination or possible undesired reactions. It is advantageous, in general, to prepare the imaging compositions shortly prior to coating them on the selected substrate. Under suitable storage conditions, which generally are conditions of darkness and reasonable avoidance of air or oxidizing atmospheres and humidity conditions, the stability of the imaging compositions is good.

In the imaging compositions, the proportions of the matrix, the imaging organo-tellurium material and the reductant precursor are variable. In those special cases where the imaging organo-tellurium material utilized is one which also inherently or concomitantly possesses desired sensitizing properties, as noted above, a separate reductant precursor is not necessary. It may, however, even in such cases, be desirable to employ a separate or added reductant precursor which may be of entirely different sensitizing properties from that inherently possessed by the particular imaging organo-tellurium material utilized. In any event, generally speaking, excluding the organic solvent or solvents, where employed as described below, at least in most cases the matrix material, which is a normally solid material, that is, solid at room temperature, will be employed in amounts in excess of any one of the other materials and will also usually be present in major amount, that is more than 50% and broadly in the range up to 90% by weight, of the total materials present in the imaging composition. The imaging organo-tellurium material, generally also a normally solid material, will ordinarily constitute from about 1 to above 20 parts per 100 parts of matrix, usually about 5-10 parts per 100 parts of matrix. The reductant precursor, where it is a separate ingredient, which is usually a solid, will usually be employed in lesser proportions, commonly of the order of about 5 to 20%, usually about 6 to 15%, by weight, of the imaging composition, although, in certain cases the proportions thereof can be substantially higher, approximately or even exceeding somewhat the proportions of the imaging organo-tellurium material. With further regard to the proportions of the aforesaid ingredients, it may be stated that the area density of the reductant precursor is desirably selected so that about 70-95% of the photons falling on the film in the region of the absorption bands of the reductant precursor are absorbed. Considerably higher concentrations of reductant precursor would leave the dark side of the film unexposed and no advantage would thus be served. In general, for optimal results in many cases, the mole concentration of the imaging organo-tellurium material should be reasonably close to or roughly approximate to that of the reductant precursor. The concentration of the polymer matrix material should be sufficient to produce an essentially amorphous film without bringing about precipitation of the imaging organo-tellurium material, the sensitizer and other supplemental ingredients when utilized. Excess polymer matrix material also tends to decrease the sensitivity of the film.

As has already been indicated, the amount of diol should be present in a concentration sufficient to provide at least 2 moles of diol for each mole of tellurium compound, and preferably to provide up to a ratio of 6:1 moles. As indicated above, our work has suggested that a complex is formed between the diol and the tellurium compound in a molar ratio of 2:1, and that excess diol above that is useful to provide a source of labile hydrogen for reaction with the reductant precursor. Larger amounts of the diol may be used if desired. To some extent, improved results are obtained when these larger amounts of diol are used; however, there is a point of diminishing returns above which increasing the amount of diol will not provide commensurate improvement in photoresponse of the finished film.

The masked reducing agent of the present invention may be present in amounts of 1% up to 200% by weight of the tellurium compounds. Measurably improved sensitivity can be found in accordance with the present invention with even very small amounts of masked reducing agent and within limitations the degree of improvement is in proportion to the amount of masked reducing agent which is incorporated in the film. Again, however, a law of diminishing returns is observed, and while large amounts of the masked reducing agent will be incorporated-in the order of 2 to 4 times the amount of tellurium compound-beyond these large amounts the increase in photoresponse obtained is not commensurate with the increased amount of masked reducing agent incorporated.

The film-forming compositions as described above will be applied to any suitable substrate. Glass, porcelain, paper and various plastic substrates have been found suitable. For the purposes of forming film-like materials, transparency is obviously desirable. For this purpose, films of polyethylene terephthalate have been found particularly suitable.

Additional considerations which those skilled in the art in formulating and using tellurium-based film compositions may utilize are apparent from U.S. Pat. No. 4,142,896, the disclosure of which is hereby incorporated by reference.

This invention is further illustrated by the following examples:

EXAMPLE 1

2.1 gms of glyceryl benzyl ether and 0.625 gms of tellurium bis-acetophenone dichloride are added to a mixture of 42 ml of methylene chloride and 58 ml of methylethyl ketone. A 2% solution of silicone oil in methylene chloride, 2.1 ml, is added to aid in preparing a smooth coating.

The mixture is stirred at room temperature for 30 minutes and then 0.625 gms of the phenyl isocyanate adduct of benzoyl hydrazine is added as a masked reducing agent. The polymeric binder (CAB-500-5, 10.42 gms) is then added, followed by 0.31 gms of 2-isopropoxynaphthoquinone.

The resulting solution was stirred in complete darkness for 1 hour and then coated on a MYLAR substrate at an average coverage of approximately 2 gms of tellurium-bis-acetylphenone dichloride per square meter. The film was then heated in an oven at 65° C. for 2-4 hours to remove the solvents.

EXAMPLE 2

2.0 gms of p-methoxy benzyl-1-glyceryl ether, and 0.625 gms tellurium-bis-acetophenone dichloride (TeBAC) were added to a mixture of 42 ml methylene chloride and 58 ml methylethyl ketone, along with 2.0 ml of a 2% solution of silicon oil in methylene chloride.

The mixture was stirred at room temperature for 30 minutes, then 0.625 gms of masked reducing agent of the formula

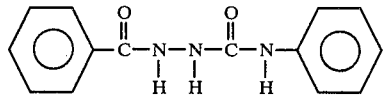

was added, and the mixture stirred for 10 minutes. The polymeric binder, Eastman CAB 500-5, in the amount of 10.42 gms, was added, followed by 0.31 gms of 2-isopropoxynaphthoquinone (IPNQ). The solution was stirred in complete darkness for 1 hour.

The resulting solution was coated in a standard meniscus coater on a substrate of 5 mil polyethylene terephthalate (Melinex type O), at a coverage approximating 2 gms of TeBAC/meter$^2$, and the resulting film heated in an oven at 65° C. for 3 hours.

When exposed to imaging energy of $10^4$ erg/cm$^2$ at 365 nm and heated to 140° C. for 30 seconds, this film gave an optical density of 2.2, with a density of 0.35 in the unimaged area. Gamma of the film was 2.0.

EXAMPLE 3

2.0 gms p-methoxy benzyl-1-glyceryl ether, and 0.625 gms of TeBAC were added to 42 ml of methylene chloride and stirred for 3 hours at 50° C. in a closed bottle. 58 ml of methyl ethyl ketone and 2 ml of 2% silicon oil in CH$_2$Cl$_2$ were added, and then the masked reducing agent, polymer, and IPNQ as in Example 2.

The mixture was stirred in darkness for 1 hour at room temperature, and coated as above.

After coating, the film was heated in an oven at 65° C. for 45 minutes. Photographic response was identical to that of the film prepared in Example 2.

EXAMPLE 4

2.5 gms o-chloro benzyl-1-glyceryl ether, and 0.600 gms tellurium-bis-acetophenone dichloride were added to a mixture of 42 ml methylene chloride and 58 ml ethyl ketone.

The mixture was stirred at room temperature for 30 minutes, then 0.625 gms of the adduct of benzoyl hydrazine and phenyl isocyanate (masked reducing agent) was added, and the mixture stirred for 10 minutes. The polymeric binder, Union Carbide VAGH in the amount of 10.42 gms, was added, followed by 0.31 gms of 2-isopropoxynaphthoquinone (IPNQ). The solution was then stirred in complete darkness for 1 hour.

The resulting solution was coated with a standard meniscus coater onto a 5 mil substrate of polyethylene terephthalate (Melinex type O), at a coverage approximating 2 gms of TeBAC/m$^2$, and the resulting film heated in an oven for 2½ hours at 65° C.

Films thus prepared exhibit an optical density of 2.0 in the image area and 0.3 in the background areas with a gamma of 3.0, when exposed to an energy of $8 \times 10^3$ erg/cm$^2$ at 365 nm and heated to 130° C. for 1 minute.

EXAMPLE 5

2.5 gms of p-benzyloxy benzyl-1-glyceryl ether, and 0.7 gms tellurium-bis-pinacolone dichloride were stirred in a mixture of 80 ml methylene chloride and 20 ml dimethyl formamide, at room temperature for 3 hours.

To this was then added 0.6 gms of masked reducing agent of the formula

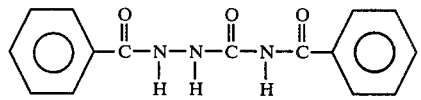

and the mixture was stirred for 10 minutes. 12 gms of the polymeric binder polyvinyl formal (Monsanto Formvar) was added, followed by 0.4 gms of 2-tert-butyl anthraquinone (BAQ). The solution was then stirred for 1 hour at room temperature in darkness.

Films were prepared by casting the solution on glass plates, with a coverage approximating 1.5 gms of organo-tellurium/m$^2$. After drying at room temperature for 1 hour, the films were heated in an oven at 65° C. for 2 hours.

Films thus prepared exhibit an optical density of 1.5 in the image area, and 0.2 in the background, and a gamma of approximately 1.5, when exposed to an imaging energy flux of $8 \times 10^4$ erg/cm$^2$ at 365 nm and heated to 110° C. for 90 seconds.

EXAMPLE 6

3.0 gms p-methoxy benzyl-1-glyceryl ether, and 1.18 gms of tellurium dichloride were stirred in 42 ml of methylene chloride and 58 ml of methyl ethyl ketone for 2 hours.

To this mixture was added 0.625 gms of benzoylhydrazine-phenylisocyanate adduct (masked reducing agent), 10.42 gms of polymeric binder, Eastman CAB 500-5, and 0.625 gms 2-isopropoxynaphthoquinone. The mixture was then stirred for 1 hour in complete darkenss at room temperature.

The mixture was then coated on a substrate of polyethylene terephthalate (Melinex type O) at a coverage approximating 3.5 gms of TeCl$_2$/m$^2$. The resulting film was heated in an oven for 3 hours at 65° C.

When exposed to an imaging energy of $10^5$ erg/cm$^2$ at 365 nm and heat processed at 150° C. for 30 seconds, these films gave an image optical density of 3.0 and a background density of 0.7. Gamma of these films was approximately 3.0.

EXAMPLE 7

0.210 gms of TeO$_2$ and 0.050 gms of TeCl$_4$ were stirred for 30 minutes in 5 ml of 2-methoxyethanol, then this mixture was added to 1.0 gms of o-chloro benzyl-1- glyceryl ether in 42 ml methylene chloride and 58 ml methyl ethyl ketone. The mixture was stirred for an additional hour. 0.625 gms of the masked reducing agent of the formula

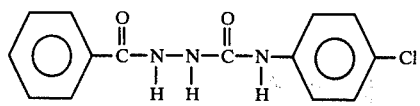

10.42 gms of polymer Eastman CAB 500-5, and 0.320 gms of 2-isopropoxynaphthoquinone were added and the mixture stirred for 1 hour.

Films were meniscus coated on 5 mil polyethylene terephthalate (Melinex type O) at a coverage of 0.4 gms $TeO_2/m^2$, and heated in an oven at 60° C. for 3 hours. The resulting films gave an optical density of 2.5 in the image area and 0.7 in the background area, and exhibited a gamma of approximately 3.5 when irradiated with an energy of $10^5$ erg/cm$^2$ at 365 nm and heat processed at 165° C. for 10 seconds.

EXAMPLE 8

0.210 gma of $TeO_2$ and 0.090 gms of TeBAC were stirred for 10 minutes in 5 ml of methoxyethanol, then this mixture was added to 2.0 gms of O-methoxy benzyl glyceryl ether in 42 ml of methylene chloride and 58 ml of methyl ethyl ketone and stirred for 1 hour. 0.550 gms of benzoyl hydrazine-phenyl isocyanate adduct (masked reducing agent), 10.42 gms of polymeric binder, Eastman CAB 500-5, and 0.300 gms of 2-isopropoxynaphthoquinone were added and the mixture stirred for 2 hours in complete darkness.

Films were meniscus coated on 5 mil polyethylene terephthalate (Melinex type O) at a coverage of 0.4 gms $TeO_2/m^2$, and heated in an oven for 3 hours at 65° C. The resulting films gave an image optical density of 2.0 and a background density of 0.5 when exposed to imaging energy of $5 \times 10^4$ erg/cm$^2$ at 365 nm and heat processed at 140° C. for 30 seconds. Gamma of these films is approximately 2.5.

EXAMPLE 9

0.480 gms of $H_2TeCl_6$ and 3.0 gms of p-methoxybenzyl-1-glyceryl ether were stirred in a mixture of 42 ml methylene chloride and 58 ml methyl ethyl ketone for 2 hours. 0.625 gms of benzoyl hydrazine-phenyl isocyanate adduct (masked reducing agent), 10.42 gms of polymer, Eastman CAB 500-5, and 0.500 gms of 2-isopropoxynaphthoquinone were added and the mixture stirred for 1 additional hour in complete darkness.

The solution was then coated on 5 mil polyethylene terephthalate (Melinex type O) at a coverage of 1.6 gms of $H_2TeCl_6/m^2$ and heated in an oven at 70° C. for 3 hours. The resulting films gave an image optical density of 1.5 and a background density of 0.1 when exposed to imaging energy of $8 \times 10^4$ erg/cm$^2$ at 365 nm and heat processed at 175° C. for 30 seconds. Gamma of these films is approximately 3.

Additional illustrations of the manner in which this invention may be practiced will be apparent from the following formulations which may be prepared and coated in a manner analogous to Examples 1 and 2:

EXAMPLE 10

.700 gms of 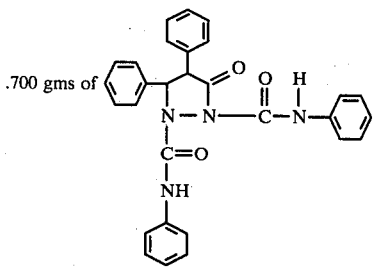

2.1 gms of p-methoxybenzyl glyceryl ether
1.0 gms of Styrene glycol
.625 gms of TeBAC
10.42 gms of Polymer CAB 500-5
58 ml of MEK
42 ml of $CH_2Cl_2$
.310 gms of IPNQ

EXAMPLE 11

.500 gms of 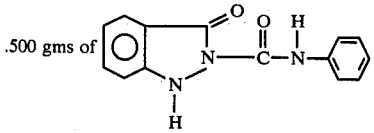

2.0 gms of o-chlorobenzyl glyceryl ether
1.0 gms of Styrene glycol
.625 gms of TeBAC
10.42 gms of CAB 500-5
58 ml of MEK
42 ml of $CH_2Cl_2$
.310 gms of IPNQ

EXAMPLE 12

.90 gms of 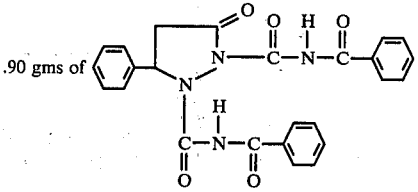

2.1 gms of o-chlorobenzyl glyceryl ether
1.0 gms of Styrene glycol
.625 gms of TeBAC
10.42 gms of CAB 500-5
58 ml of MEK
42 ml of $CH_2Cl_2$
.310 gms of IPNQ

EXAMPLE 13

1.0 gms of 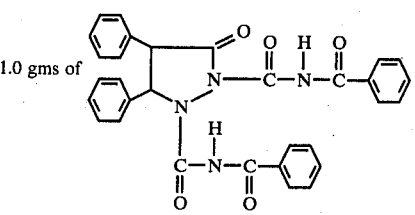

EXAMPLE 14

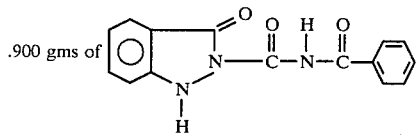

2.1 gms of o-chlorobenzyl glyceryl ether
1.0 gms of Styrene glycol
.625 gms of TeBAC
10.42 gms of CAB 500-5
58 ml of MEK
42 ml of $CH_2Cl_2$
.310 gms of IPNQ

EXAMPLE 15

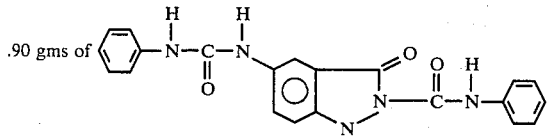

2.1 gms of o-chlorobenzyl glyceryl ether
1.0 gms of Styrene glycol
.625 gms of TeBAC
10.42 gms of CAB 500-5
58 ml of MEK
42 ml of $CH_2Cl_2$
.310 gms of IPNQ

We claim:

1. In a composition responsive to activating energy for forming an imaging film, which composition comprises
(a) an image-forming tellurium compound;
(b) a reductant precursor which will abstract labile hydrogen from a hydrogen donor under the influence of activating radiation to become a reducing agent with respect to the image-forming tellurium compound;
(c) a source of labile hydrogen for reaction with said reductant precursor; and
(d) a matrix in which said tellurium compound, reductant precursor and source of labile hydrogen are combined in amounts effective to form a composition which may be applied to a substrate,
the improvement wherein there is included in said composition a masked reducing agent of the formula $R^1$—NY—$NY_2$;

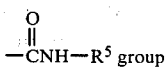

wherein $R^1$ is alkyl, alkanoyl, alkoxycarbonyl, phenyl, benzyl, benzoyl, nitrophenyl, benzylcarbonyl, diphenylmethyl, diphenylethyl, diphenylpropylcarbonyl or amino carbonyl; $R^2$, $R^3$ and $R^4$ each and independently are hydrogen, alkyl, phenyl, or amino; and $R^5$ is phenyl, nitrophenyl, halophenyl, alkyl, mono-, di- or tri-haloacetyl, benzoyl, alkylphenyl, or alkyl-p-isocyanophenyl,
said alkyl grouping in the radicals $R^1$ through $R^5$ having from 1 to 7 carbon atoms,
and wherein Y is hydrogen or $$-\overset{O}{\underset{\|}{C}}NH-R^5,$$

said compound containing at least one $$-\overset{O}{\underset{\|}{C}}NH-R^5 \text{ group}$$

in said compound,
the amount of said masked reducing agent being at least 1% by weight of said image-forming tellurium compound.

2. The improved image-forming composition according to claim 1, wherein there is additionally provided a diol of the formula $$R^{10}-\underset{\underset{OH}{|}}{\overset{\overset{H}{|}}{C}}-Z-\underset{\underset{OH}{|}}{\overset{\overset{H}{|}}{C}}-R^{11}$$

wherein each of $R^{10}$ and $R^{11}$ independently represents hydrogen, a hydrocarbon group, including straight chain, branched chain and cyclic hydrocarbon groups, hydroxyalkyl groups, alkoxycarbonyl groups, cycloalkyl groups or aryl groups; and Z represents a direct C-C bond between the carbon atoms on either side of it, or an arylene group, the group (—C≡C—), the group (—$CR^{12}$=$CR^{13}$)$_n$, wherein n represents 1 or 2, and each of $R^{12}$ and $R^{13}$ represents hydrogen or an alkyl group or taken from part of a carbocyclic or heterocyclic ring, said diol being provided in an amount equivalent to at least 2 moles thereof per 1 mole of said tellurium forming compound.

3. The improved image-forming composition according to claim 1, wherein there is provided a diol of the formula $R^7$-X-$CH_2$-CHOH-$CH_2OH$ wherein $R^7$ is alkyl, alkanoyl, thiazolinyl, alkenyl, benzyl, alkylbenzyl, alkoxybenzyl, hydroxyalkylbenzyl, and halobenzyl; the alkyl radical having from 1 to 7 carbon atoms; and X is oxygen or sulphur.

4. The improved image-forming composition according to claim 1, wherein said tellurium compound is selected from the group consisting of

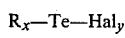

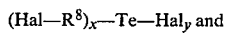

in the foregoing formulae, R being an organic radical containing at least 1 carbonyl group, $R^8$ being the residue of an ethyleneic hydrocarbon, Hal being halogen, x being 1, 2 or 3; and x+y=4; n being an integer from 1 to 4 and m+n=4.

5. The improved image-forming composition according to claim 3, wherein said tellurium compound is selected from the group consisting of

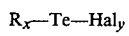

in the foregoing formulae, R being an organic radical containing at least 1 carbonyl group, $R^8$ being the residue of an ethyleneic hydrocarbon; Hal being halogen, x being 1, 2 or 3, and x+y=4; n being an integer from 1 to 4 and m+n=4.

6. The improved image-forming composition according to claim 4 wherein said reductant precursor is selected from the group consisting of 2-isopropoxynaphthoquinone; 2-t-butyl-anthraquinone; 1,10-phenanthrenequinone; 1,1'-dibenzoylferrocene; 1-phenyl-1,2-propanedione; 2-hydroxy-1,4-naphthoquinone; benzil; furil; diacetylferrocene; acetylferrocene; 1,4-bis (phenyl glyoxal) benzene; o-naphthoquinone; 4,5-pyrinequinone; 4,5,9,10-pyrinequinone; benzophenone; acetophenone; 1,5-diphenyl-1,3,5-pentanetrione; ninhydrin; 4,4'-dibromobenzophenone; 1,8-dichloroanthraquinone; 1,2-benzanthraquinone; 2-methylanthraquinone; 1-chloroanthraquinone; 7,8,9,10-tetrahydronaphthacenequinone; 9,10-anthraquinone; and 1,4-dimethylanthraquinone.

7. The improved image-forming compound according to claim 5 wherein said reductant precursor is selected from the group consisting of 2-isopropoxynaphthoquinone; 2-t-butylanthraquinone; 1,10-phenanthrenequinone; 1,1'-dibenzoylferrocene; 1-phenyl-1,2-propanedione; 2-hydroxy-1,4-naphthoquinone; benzil; furil; diacetylferrocene; acetylferrocene; 1,4-bis (phenyl glyoxal) benzene; o-naphthoquinone; 4,5-pyrinequinone; 4,5,9,10-pyrinequinone; benzophenone; acetophenone; 1,5-diphenyl-1,3,5-pentanetrione; ninhydrin; 4,4'-dibromobenzophenone; 1,8-dichloroanthraquinone; 1,2-benzanthraquinone; 2-methylanthraquinone; 1-chloroanthraquinone; 7,8,9,10-tetrahydronaphthacenequinone; 9,10-anthraquinone; and 1,4-dimethylanthraquinone.

8. The improved image-forming composition according to one of claims 1-7 wherein said masked reducing agent is

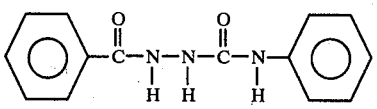

9. The improved image-forming composition according to one of claims 1-7 wherein said masked reducing agent is

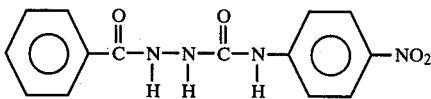

10. The improved image-forming composition according to one of claims 1-7 wherein said masked reducing agent is

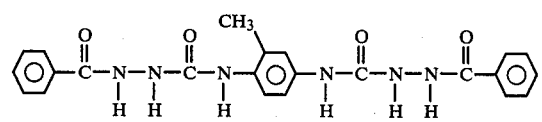

11. The improved image-forming composition according to one of claims 1-7 wherein said masked reducing agent is

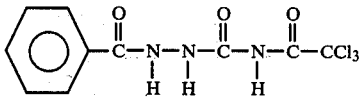

12. The improved image-forming composition according to one of claims 1-7 wherein said masked reducing agent is

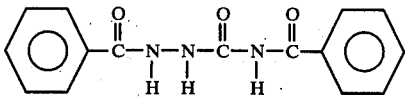

13. The improved image-forming composition according to one of claims 1-7 wherein said masked reducing agent is

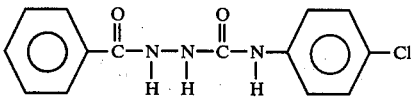

14. The improved image-forming composition according to one of claims 1-7 wherein said masked reducing agent is

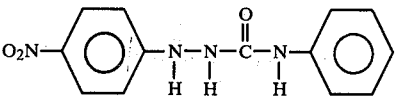

15. The improved image-forming composition according to one of claims 1-7 wherein said masked reducing agent is

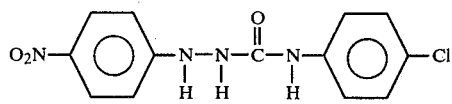

16. The improved image-forming composition according to one of claims 1–7 wherein said masked reducing agent is

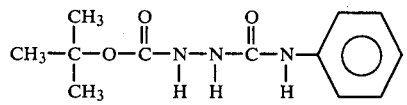

17. The improved image-forming composition according to one of claims 1–7 wherein said masked reducing agent is

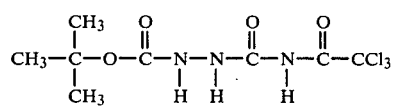

18. The improved image-forming composition according to one of claims 1–7 wherein said masked reducing agent is

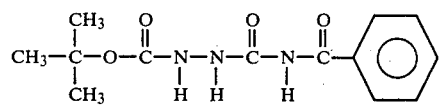

19. The improved image-forming composition according to one of claims 1–7 wherein said masked reducing agent is

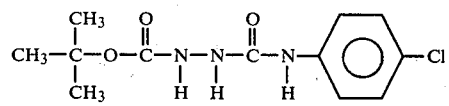

20. The improved image-forming composition according to one of claims 1–7 wherein said masked reducing agent is

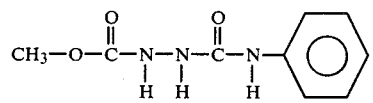

21. The improved image-forming composition according to one of claims 1–7 wherein said masked reducing agent is

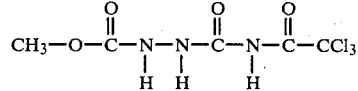

22. The improved image-forming composition according to one of claims 1–7 wherein said masked reducing agent is

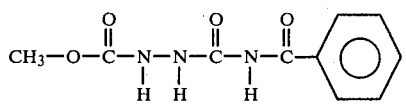

23. The improved image-forming composition according to one of claims 1–7 wherein said masked reducing agent is

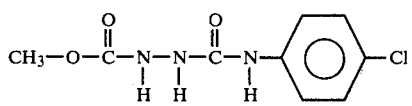

24. The improved image-forming composition according to one of claims 1–7 wherein said masked reducing agent is

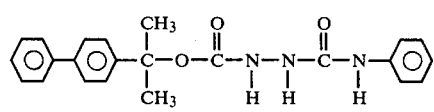

25. The improved image-forming composition according to one of claims 1–7 wherein said masked reducing agent is

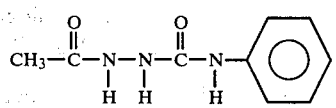

26. The improved image-forming composition according to one of claims 1–7 wherein said masked reducing agent is

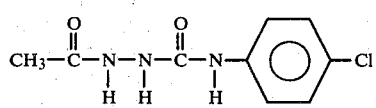

27. The improved image-forming composition according to one of claims 1–7 wherein said masked reducing agent is

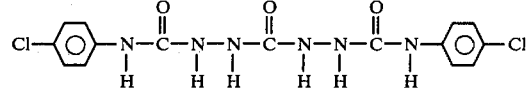

28. The improved image-forming composition according to one of claims 1–7 wherein said masked reducing agent is

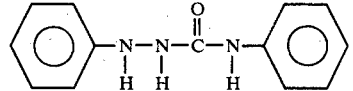

29. The improved image-forming composition according to one of claims 1–7 wherein said masked reducing agent is

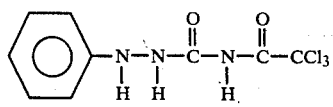

30. The improved image-forming composition according to one of claims 1-7 wherein said masked reducing agent is

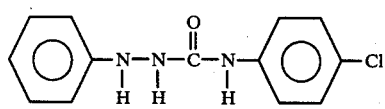

31. The improved image-forming composition according to one of claims 1-7 wherein said masked reducing agent is

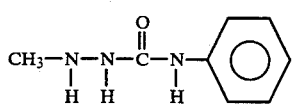

32. The improved image-forming composition according to one of claims 1-7 wherein said masked reducing agent is

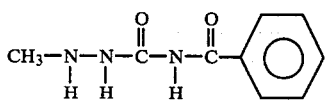

33. The improved image-forming composition according to one of claims 1-7 wherein said masked reducing agent is

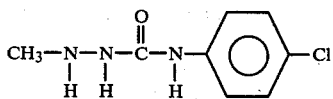

34. The improved image-forming composition according to one of claims 1-7 wherein said masked reducing agent is

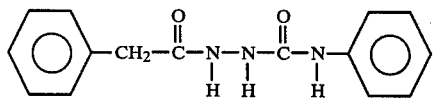

35. The improved image-forming composition according to one of claims 1-7 wherein said masked reducing agent is

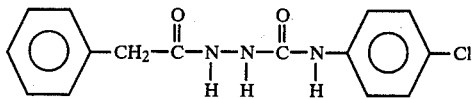

36. The improved image-forming composition according to one of claims 1-7 wherein said masked reducing agent is

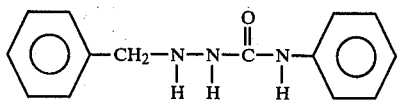

37. The improved image-forming composition according to one of claims 1-7 wherein said masked reducing agent is

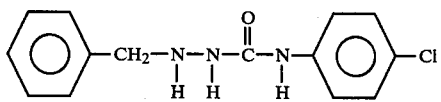

38. The improved image-forming composition according to one of claims 1-7 wherein said masked reducing agent is

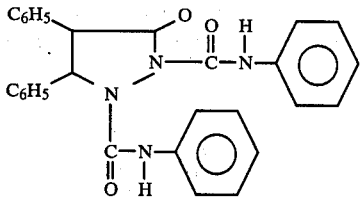

39. The improved image-forming composition according to one of claims 1-7 wherein said masked reducing agent is

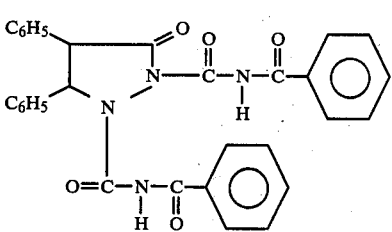

40. The improved image-forming composition according to one of claims 1-7 wherein said masked reducing agent is

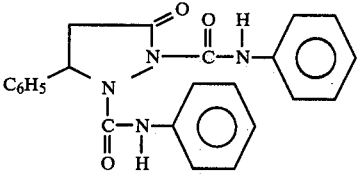

41. The improved image-forming composition according to one of claims 1-7 wherein said masked reducing agent is

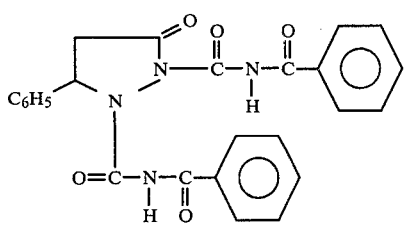

42. The improved image-forming composition according to one of claims 1-7 wherein said masked reducing agent is

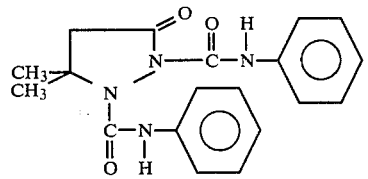

43. The improved image-forming composition according to one of claims 1-7 wherein said masked reducing agent is

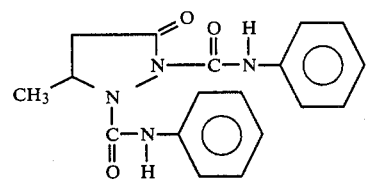

44. The improved image-forming composition according to one of claims 1-7 wherein said masked reducing agent is

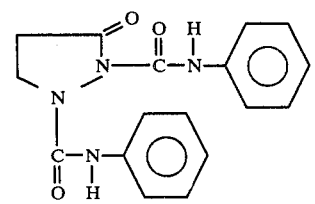

45. The improved image-forming composition according to one of claims 1-7 wherein said masked reducing agent is

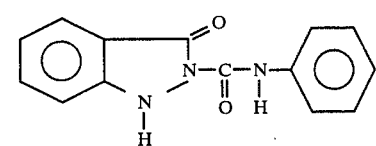

46. The improved image-forming composition according to one of claims 1-7 wherein said masked reducing agent is

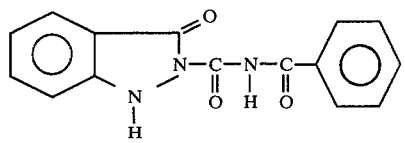

47. The improved image-forming composition according to one of claims 1-7 wherein said masked reducing agent is

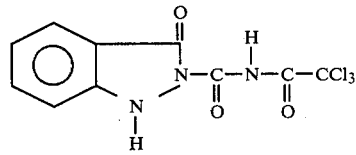

48. The improved image-forming composition according to one of claims 1-7 wherein said masked reducing agent is

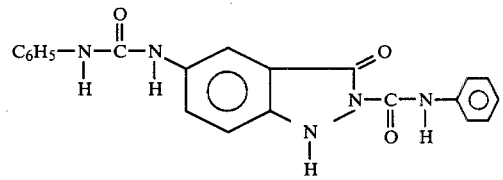

49. In a film for forming an image comprising a composition on a substrate wherein said composition contains
   (a) an image-forming tellurium compound;
   (b) a reductant precursor which will abstract labile hydrogen from a hydrogen donor under the influence of activating radiation to become a reducing agent with respect to the image-forming tellurium compound;
   (c) a source of labile hydrogen for reaction with said reductant precursor; and
   (d) a matrix in which said tellurium compound, reductant precursor and source of labile hydrogen are combined in amounts effective to form a composition which may be applied to a substrate,
   the improvement wherein there is provided in said emulsion a masked reducing agent of the formula

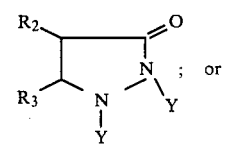

; or

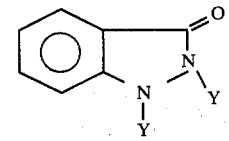

wherein $R^1$ is alkyl, alkanoyl, alkoxycarbonyl, phenyl, benzyl, benzoyl, nitrophenyl, benzylcarbonyl, diphenylmethyl, diphenylethyl, diphenylpropylcarbonyl or amino carbonyl; $R^2$, $R^3$ and $R^4$ each and independently are hydrogen, alkyl, phenyl, or amino; and R⁵ is phenyl, nitrophenyl, halophenyl, alkyl, mono-, di- or tri-haloalkyl, benzoyl, alkylphenyl, or alkyl-p-isocyanophenyl, said alkyl grouping in the radicals $R^1$ through $R^5$ having from 1 to 7 carbon atoms; and wherein Y is hydrogen or

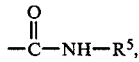

said compound containing at least one

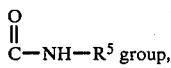 group, the amount of said masked reducing agent being at least 1% by weight of said image-forming tellurium compound.

50. The improved film according to claim 49, wherein there is additionally provided a diol of the formula

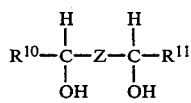

wherein each of $R^{10}$ and $R^{11}$ independently represents hydrogen, a hydrocarbon group, including straight chain, branched chain and cyclic hydrocarbon groups, hydroxyalkyl groups, alkoxycarbonyl groups, cycloalkyl groups or aryl groups; and Z represents a direct C—C bond between the carbon atoms on either side of it, or the group (—C≡C—), the group $(-CR^{12}=CR^{13})_n$, wherein n represents a whole number, for example, 1 or 2, and each of $R^{12}$ and $R^{13}$ represents hydrogen or an alkyl group or taken from part of a carbocyclic or heterocyclic ring, said diol being provided in an amount equivalent to at least 2 moles thereof per 1 mole of said tellurium forming compound.

51. The improved film according to claim 49 wherein there is provided a diol of the formula $$R^7-X-CH_2-CHOH-CH_2OH$$

wherein $R^7$ is alkyl, alkanoyl, thiazolinyl, alkenyl, benzyl, alkylbenzyl, alkoxybenzyl, hydroxyalkylbenzyl, and halobenzyl; the alkyl radical having from 1 to 7 carbon atoms; and X is oxygen or sulphur.

52. The improved film according to claim 49, 50 or 51, wherein said tellurium compound is selected from the group consisting of

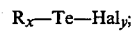

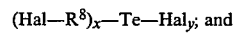

in the foregoing formulae, R being an organic radical containing at least one carbonyl group, $R^8$ being the residue of an ethyleneic hydrocarbon, Hal being halogen, x being 1, 2 or 3; and x+y=4; n being an integer from 1 to 4 and m+n=4.

53. The improved film according to claim 52 wherein said reductant precursor is selected from the group consisting of 2-isopropoxynaphthoquinone; 2-t-butylanthraquinone; 1,10-phenanthrenequinone; 1,1'-dibenzoylferrocene; 1-phenyl-1,2-propanedione; 2-hydroxy-1,4-naphthoquinone; benzil; furil, diacetylferrocene; acetylferrocene; 1,4-bis (phenyl glyoxal) benzene; o-naphthoquinone; 4,5-pyrinequinone; 4,5,9,10-pyrinequinone; benzophenone; acetophenone; 1,5-diphenyl-1,3,5-pentanetrione; ninhydrin; 4,4'-dibromobenzophenone; 1,8-dichloroanthraquinone; 1,2-benzanthraquinone; 2-methylanthraquinone; 1-chloroanthraquinone; 7,8,9,10-tetrahydronaphthacenequinone; 9,10-anthraquinone; and 1,4-dimethylanthraquinone.

54. The improved film according to claim 53 wherein said reductant precursor is selected from the group consisting of 2-isopropoxynaphthoquinone; 2-t-butylanthraquinone; 1,10-phenanthrenequinone; 1,1'-dibenzoylferrocene; 1-phenyl-1,2-propanedione; 2-hydroxy-1,4-naphthoquinone; benzil; furil; diacetylferrocene; acetylferrocene; 1,4-bis (phenyl glyoxal) benzene; o-naphthoquinone; 4,5-pyrinequinone; 4,5,9,10-pyrinequinone; benzophenone; acetophenone; 1,5-diphenyl-1,3,5-pentanetrione; ninhydrin; 4,4'-dibromobenzophenone; 1,8-dichloroanthraquinone; 1,2-benzanthraquinone; 2-methyl-anthraquinone; 1-chloroanthraquinone; 7,8,9,10-tetrahydronaphthacenequinone; 9,10-anthraquinone; and 1,4-dimethylanthraquinone.

55. In a method for recording electromagnetic radiation, wherein said radiation impinges imagewise upon a photosensitive film to produce a change in at least one property thereof, which film is a photosensitive composition carried by a substrate, the photosensitive composition containing (a) an image-forming tellurium compound;

(b) a reductant precursor which will abstract labile hydrogen from a hydrogen donor under the influence of activating radiation to become a reducing agent with respect to the image-forming tellurium compound;

(c) a source of labile hydrogen for reaction with said reductant precursor; and (d) a matrix in which said tellurium compound, reductant precursor and source of labile hydrogen are combined in amounts effective to form a photosensitive composition which may be applied to a substrate, the improvement wherein there is included in said photosensitive composition a masked reducing agent of the formula

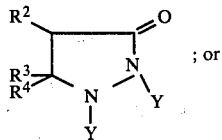

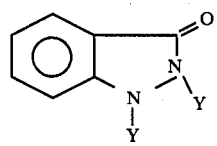

wherein $R^1$ is alkyl, alkanoyl, alkoxycarbonyl, phenyl, benzyl, benzoyl, nitrophenyl, benzylcarbonyl, diphenylmethyl, diphenylethyl, diphenylpropylcarbonyl or amino carbonyl; $R^2$, $R^3$ and $R^4$ each and independently are hydrogen, alkyl, phenyl, or amino; and R⁵ is phenyl, nitrophenyl, halophenyl, alkyl, mono-, di- or tri-haloacetyl, benzoyl, alkylphenyl, or alkyl-p-isocyanophenyl, said alkyl grouping in the radicals R¹ through R⁵ having from 1 to 7 carbon atoms, and wherein Y is H or $$-\overset{O}{\underset{\|}{C}}-NHR^5,$$

there being at least one $$-\overset{O}{\underset{\|}{C}}-NH-R^5 \text{ group}$$

in said compound;

the amount of said masked reducing agent being at least 1% by weight of said image-forming tellurium compound.

56. The improved method according to claim 56, wherein there is included in said photosensitive composition a diol of the formula $$R^{10}-\overset{H}{\underset{OH}{\overset{|}{C}}}-Z-\overset{H}{\underset{OH}{\overset{|}{C}}}-R^{11}$$

wherein each of R¹⁰ and R¹¹ independently represents hydrogen, a hydrocarbon group, including straight chain, branched chain and cyclic hydrocarbon groups, hydroxyalkyl groups, alkoxycarbonyl groups, cycloalkyl groups or aryl groups; and Z represents a direct C—C bond between the carbon atoms on either side of it, or an arylene group, the group (—C≡C—), the group (—CR¹²=CR¹³)ₙ, wherein n represents a whole number, for example 1 or 2, and each of R¹² and R¹³ represents hydrogen or an alkyl group or taken from part of a carbocyclic or heterocyclic ring, said diol being provided in an amount equivalent to at least 2 moles thereof per 1 mole of said tellurium forming compound.

57. The improved method according to claim 55, wherein there is included in said photosensitive composition a diol of the formula $$R^7-X-CH_2-CHOH-CH_2OH$$

wherein R⁷ is alkyl, alkanoyl, thiazolinyl, alkenyl, benzyl, alkylbenzyl, alkoxybenzyl, hydroxyalkylbenzyl, and halobenzyl; the alkyl radical having from 1 to 7 carbon atoms; and X is oxygen or sulphur.

58. The improved method according to claim 56, wherein there is included in said photosensitive composition a tellurium compound selected from the group consisting of $$R_x-Te-Hal_y;$$

$$(Hal-R^8)_x-Te-Hal_y; \text{ and}$$

$$TeCl_nBr_m$$

in the foregoing formulae, R being an organic radical containing at least one carbonyl group, R⁸ being the residue of an ethyleneic hydrocarbon, Hal being halogen, x being 1, 2 or 3; and x+y=4, n being an integer from 1 to 4 and m+n=4.

59. The improved method according to claim 57, wherein there is included in said photosensitive composition a tellurium compound selected from the group consisting of $$R_x-Te-Hal_y;$$

$$(Hal-R^8)_x-Te-Hal_y; \text{ and}$$

$$TeCl_nBr_m$$

in the foregoing formulae, R being an organic radical containing at least one carbonyl group, R⁸ being the residue of an ethyleneic hydrocarbon, Hal being halogen, x being 1, 2 or 3, and x+y=4; n being an integer from 1 to 4, and m+n=4.

60. The improved method according to claim 58, wherein there is included in said photosensitive composition a reductant precursor selected from the group consisting of 2-isopropoxynaphthoquinone; 2-t-butylanthraquinone; 1,10-phenanthrenequinone; 1,1'-dibenzoylferrocene; 1-phenyl-1,2-propanedione; 2-hydroxy-1,4-naphthoquinone; benzil; furil; diacetylferrocene; acetylferrocene; 1,4-bis (phenyl glyoxal) benzene; o-naphthoquinone; 4,5-pyrinequinone; 4,5,9,10-pyrinequinone; benzophenone; acetophenone; 1,5-diphenyl-1,3,5-pentanetrione; ninhydrin; 4,4'-dibromobenzophenone; 1,8-dichloroanthraquinone; 1,2-benzanthraquinone; 2-methylanthraquinone; 1-chloroanthraquinone; 7,8,9,10-tetrahydronaphthacenequinone; 9,10-anthraquinone; and 1,4-dimethylanthraquinone.

61. The improved method according to claim 59, wherein there is included in said photosensitive composition a reductant precursor selected from the group consisting of 2-isopropoxynaphthoquinone; 2-t-butylanthraquinone; 1,10-phenanthrenequinone; 1,1'-dibenzoylferrocene; 1-phenyl-1,2-propanedione; 2-hydroxy-1,4-naphthoquinone; benzil; furil; diacetylferrocene; acetylferrocene; 1,4-bis (phenyl glyoxal) benzene; o-naphthoquinone; 4,5-pyrinequinone; 4,5,9,10-pyrinequinone; benzophenone; acetophenone; 1,5-diphenyl-1,3,5-pentanetrione; ninhydrin; 4,4'-dibromobenzophenone; 1,8-dichloroanthraquinone; 1,2-benzanthraquinone; 2-methylanthraquinone; 1-chloroanthraquinone; 7,8,9,10-tetrahydronaphthacenequinone; 9,10-anthraquinone; and 1,4-dimethylanthraquinone.

62. In an imaging method employing a reducible tellurium compound which may be decomposed by electrons to form tellurium and by-products reactive with amides, the tellurium compound being disposed in a film-like layer, the improvement comprising subjecting said layer imagewise to an activating energy in the form of free electrons having sufficient energy to reduce said tellurium compounds to free tellurium and by-products reactive with amides, and including in said film-like layer a masked reducing agent of the formula $$R^1-NY-NY_2;$$

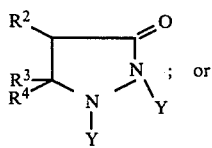

; or

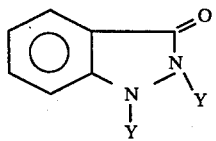

wherein R¹ is alkyl, alkanoyl, alkoxycarbonyl, phenyl, benzyl, benzoyl, nitrophenyl, benzylcarbonyl, diphenylmethyl, diphenylethyl, diphenylpropylcarbonyl or amino carbonyl; R², R³ and R⁴ each and independently are hydrogen, alkyl, phenyl, or amino; and R⁵ is phenyl, nitrophenyl, halophenyl, alkyl, mono-, di- or tri-haloacetyl, benzoyl, alkylphenyl, or alkyl-p-isocyanophenyl, said alkyl grouping in the radicals R¹ through R⁵ having from 1 to 7 carbon atoms, and wherein Y is hydrogen or

said compound containing at least one

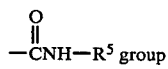

in said compound,
the amount of said masked reducing agent being at least 1% by weight of said image-forming tellurium compound.

63. The improved method according to claim 62, wherein there is additionally provided in said film-like layer a diol of the formula

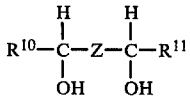

wherein each of R¹⁰ and R¹¹ independently represents hydrogen, a hydrocarbon group, including straight chain, branched chain and cyclic hydrocarbon groups, hydroxyalkyl groups, alkoxycarbonyl groups, cycloalkyl groups or aryl groups; and Z represents a direct C—C bond between the carbon atoms on either side of it, or an arylene group, the group (—C≡C—), the group (—CR¹²=CR¹³)$_n$, wherein n represents 1 or 2, and each of R¹² and R¹³ represents hydrogen or an alkyl group or taken from part of a carbocyclic or heterocyclic ring, said diol being provided in an amount equivalent to at least 2 moles thereof per 1 mole of said tellurium forming compound.

64. The improved method according to claim 62 wherein there is included within said film-like layer a diol of the formula

R⁷—X—CH₂—CHOH—CH₂OH wherein R⁷ is alkyl, alkanoyl, thiazolinyl, alkenyl, benzyl, alkylbenzyl, alkoxybenzyl, hydroxyalkylbenzyl, and halobenzyl; the alkyl radical having from 1 to 7 carbon atoms; and X is oxygen or sulphur.

65. The improved method according to claim 62, 63 or 64, wherein said tellurium compound is selected from the group consisting of

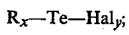

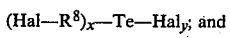

in the foregoing formulae, R being an organic radical containing at least 1 carbonyl group, R⁸ being the residue of an ethyleneic hydrocarbon, Hal being halogen, x being 1, 2 or 3; and x+y=4; n being an integer from 1 to 4 and m+n=4.

* * * * *